US012582759B2

(12) United States Patent
     Ingram et al.

(10) Patent No.:  US 12,582,759 B2
(45) Date of Patent:      Mar. 24, 2026

(54) NEGATIVE PRESSURE CHARGED VIBRATION MECHANISM FOR INTERMITTENT WOUND DRESSING VIBRATION

(71) Applicant: Solventum Intellectual Properties Company, Maplewood, MN (US)

(72) Inventors: Shannon C. Ingram, Bulverde, TX (US); Christopher Allen Carroll, San Antonio, TX (US); Benjamin Andrew Pratt, Poole (GB); Justin Rice, Denver, CO (US)

(73) Assignee: Solventum Intellectual Properties Company, Maplewood, MN (US)

( * ) Notice: Subject to any disclaimer, the term of this patent is extended or adjusted under 35 U.S.C. 154(b) by 1056 days.

(21) Appl. No.: 17/640,011

(22) PCT Filed: Sep. 2, 2020

(86) PCT No.: PCT/IB2020/058166
     § 371 (c)(1),
     (2) Date: Mar. 3, 2022

(87) PCT Pub. No.: WO2021/044307
     PCT Pub. Date: Mar. 11, 2021

(65) Prior Publication Data
     US 2022/0323667 A1      Oct. 13, 2022

Related U.S. Application Data

(60) Provisional application No. 62/895,722, filed on Sep. 4, 2019.

(51) Int. Cl.
     A61M 1/00          (2006.01)
     A61B 17/32         (2006.01)
     (Continued)

(52) U.S. Cl.
     CPC ....... A61M 1/75 (2021.05); A61B 17/320068 (2013.01); A61M 1/915 (2021.05);
     (Continued)

(58) Field of Classification Search
     CPC ........ A61M 1/75; A61M 1/915; A61M 1/985; A61M 1/90; A61M 1/91; A61M 1/962;
     (Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion for Corresponding Application No. PCT/IB2020/058166 mailed Nov. 4, 2020.
(Continued)

*Primary Examiner* — Jessica Arble
*Assistant Examiner* — Eric Rassavong

(57)                    ABSTRACT

A system, apparatus and method for delivering negative pressure and vibrations proximate a wound site. The system comprises a dressing adapted to be fluidly coupled to the wound site and further adapted to translate vibrations to the wound site. A pad is coupled to a negative pressure source and to the dressing. The pad is also coupled to a vibration module. The system further comprises a drape covering the dressing and the pad and forming a seal between the wound site and the environment. The vibration module fluidly couples to the dressing and provides vibrations during application of negative pressure.

16 Claims, 10 Drawing Sheets

(51) Int. Cl.
    *A61F 13/05*     (2024.01)
    *A61M 27/00*     (2006.01)

(52) U.S. Cl.
    CPC ... *A61M 1/985* (2021.05); *A61B 2017/32007*
        (2017.08); *A61F 13/05* (2024.01); *A61M 1/90*
        (2021.05); *A61M 1/91* (2021.05); *A61M 1/962*
        (2021.05); *A61M 1/98* (2021.05); *A61M 27/00*
        (2013.01); *A61M 2205/3344* (2013.01)

(58) Field of Classification Search
    CPC .................. A61M 1/98; A61M 27/00; A61M
        2205/3344; A61M 2205/103; A61M
        2205/106; A61B 17/320068; A61B
        2017/32007; A61F 13/05; A61F 11/045;
        A61H 23/0263; A61H 23/02; H01H
        35/38; H01H 35/2614; H01H 35/346;
        H01H 35/00
    See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2014/0163491 A1 | 6/2014 | Schuessler et al. |
| 2015/0080788 A1 | 3/2015 | Blott et al. |
| 2015/0094674 A1* | 4/2015 | Pratt ...................... A61M 1/96 |
| | | 604/319 |
| 2018/0303515 A1* | 10/2018 | Shadduck ...... A61B 17/320068 |

FOREIGN PATENT DOCUMENTS

| | | | |
|---|---|---|---|
| AU | 755496 | B2 | 12/2002 |
| CA | 2005436 | A1 | 6/1990 |
| DE | 26 40 413 | A1 | 3/1978 |
| DE | 43 06 478 | A1 | 9/1994 |

(56) References Cited

FOREIGN PATENT DOCUMENTS

| | | | | | |
|---|---|---|---|---|---|
| DE | 29 504 378 | U1 | 9/1995 | | |
| EP | 0100148 | A1 | 2/1984 | | |
| EP | 0117632 | A2 | 9/1984 | | |
| EP | 0161865 | A2 | 11/1985 | | |
| EP | 0358302 | A2 | 3/1990 | | |
| EP | 1018967 | A1 | 7/2000 | | |
| GB | 692578 | A | 6/1953 | | |
| GB | 2195255 | A | 4/1988 | | |
| GB | 2 197 789 | A | 6/1988 | | |
| GB | 2 220 357 | A | 1/1990 | | |
| GB | 2 235 877 | A | 3/1991 | | |
| GB | 2 329 127 | A | 3/1999 | | |
| GB | 2 333 965 | A | 8/1999 | | |
| JP | 4129536 | B2 | 8/2008 | | |
| SG | 71559 | | 4/2002 | | |
| WO | 80/02182 | A1 | 10/1980 | | |
| WO | 87/04626 | A1 | 8/1987 | | |
| WO | 90/010424 | A1 | 9/1990 | | |
| WO | 93/009727 | A1 | 5/1993 | | |
| WO | 94/20041 | A1 | 9/1994 | | |
| WO | 96/05873 | A1 | 2/1996 | | |
| WO | 97/18007 | A1 | 5/1997 | | |
| WO | 99/13793 | A1 | 3/1999 | | |
| WO | WO-2005105175 | A1 * | 11/2005 | .......... | A61M 1/0058 |
| WO | 2010093753 | A1 | 8/2010 | | |
| WO | WO-2016061655 | A1 * | 4/2016 | ............. | E21B 41/00 |
| WO | WO-2017087687 | A1 * | 5/2017 | ............ | A61M 1/732 |
| WO | WO-2018211500 | A1 * | 11/2018 | ............ | A61M 1/916 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, Md., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract,

(56)  References Cited

OTHER PUBLICATIONS editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

NEGATIVE PRESSURE CHARGED VIBRATION MECHANISM FOR INTERMITTENT WOUND DRESSING VIBRATION

CROSS-REFERENCE TO RELATED APPLICATIONS

This application claims the benefit of priority to U.S. Provisional Application No. 62/895,722, filed on Sep. 4, 2019, which is incorporated herein by reference in its entirety.

TECHNICAL FIELD

The invention set forth in the appended claims relates generally to tissue treatment systems and more particularly, but without limitation, to a negative pressure charged vibration mechanism for creating vibrations proximate a wound site.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for imparting vibration in a negative-pressure therapy environment are set forth in the appended claims. Illustrative embodiments are also provided to enable a person skilled in the art to make and use the claimed subject matter.

For example, in some embodiments, a passive mechanism is provided that generates low or high frequency vibrations and is coupled to a dressing placed proximate a sealed wound site. The vibrations may be created by a diaphragm that moves in response to changes in negative pressure inside the mechanism. The movement of the diaphragm in the mechanism may generate a mechanical force that may be translated to the dressing and the wound site.

More generally, a system for delivering negative pressure and vibrations proximate a wound site is provided. The system comprises a dressing adapted to be fluidly coupled to the wound site and further adapted to translate vibrations to the wound site. A pad is coupled via a pressure port to a negative pressure source and to the dressing. The pad has a vibration frame and an opening in the vibration frame for fluidly coupling to the wound site. The system further comprises a drape covering the dressing and the pad and forming a seal between the wound site and the environment. The drape further defines an opening for exposure of the vibration frame to the environment. A vibration module is provided and supported by the vibration frame. The vibration module fluidly couples to the dressing and provides vibrations during operation.

Alternatively, other example embodiments may comprise an apparatus for delivering negative pressure and vibrations proximate a wound site. The apparatus includes a pad coupled to a negative pressure source and to a dressing. A drape covers the dressing and the pad and forms a seal between the wound site and the environment. A vibration module is coupled to the pad and the dressing and is adapted to provide vibrations.

Another example embodiment is a method for delivering negative pressure and vibrations proximate a wound site. The method provides a dressing fluidly coupled to a wound site. A pad is coupled to a negative pressure source and the dressing, and has a vibration frame thereon. The dressing and pad are covered with a drape to seal the wound site from the environment. Activation of the negative pressure source induces vibrations in a vibration module coupled to the pad and provides vibrations to the pad, the dressing and the wound site.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
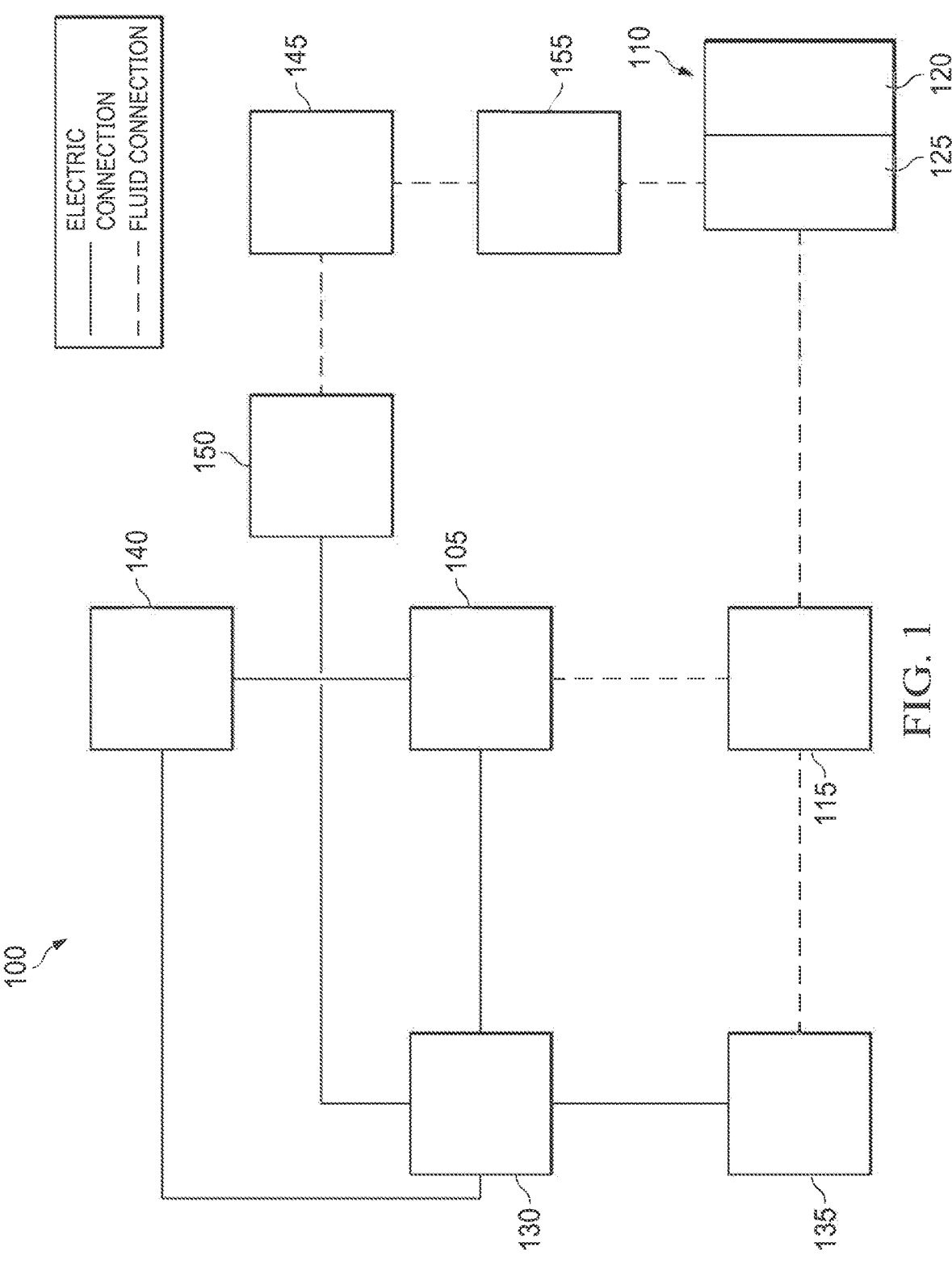
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source [such as a positive-pressure source 150, a negative-pressure source such as the negative-pressure source 105, or both] in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source 145 during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. For example, the tensile strength of foam may be increased for instillation of topical treatment solutions. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITE-FOAM™ dressing available from Kinetic Concepts, Inc. of San Antonio, Texas Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 g/m²/24 hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

Figure 2:
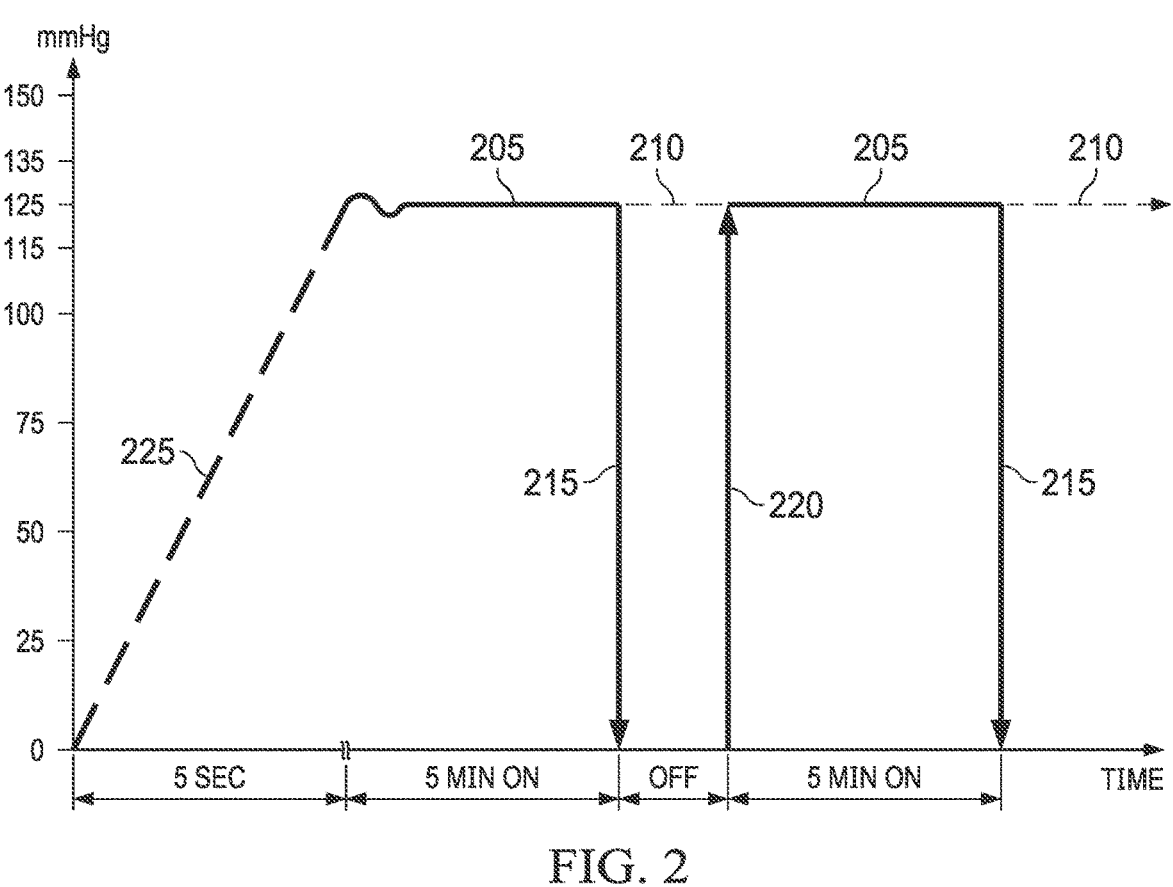
FIG. 2 is a graph illustrating additional details of example pressure control modes that may be associated with some embodiments of the therapy system of FIG. 1.

FIG. 2 is a graph illustrating additional details of an example control mode that may be associated with some embodiments of the controller 130. In some embodiments, the controller 130 may have a continuous pressure mode, in which the negative-pressure source 105 is operated to provide a constant target negative pressure, as indicated by line 205 and line 210, for the duration of treatment or until manually deactivated. Additionally or alternatively, the controller may have an intermittent pressure mode, as illustrated in the example of FIG. 2. In FIG. 2, the x-axis represents time and the y-axis represents negative pressure generated by the negative-pressure source 105 over time. In the example of FIG. 2, the controller 130 can operate the negative-pressure source 105 to cycle between a target pressure and atmospheric pressure. For example, the target pressure may be set at a value of 135 mmHg, as indicated by line 205, for a specified period of time (e.g., 5 min), followed by a specified period of time (e.g., 2 min) of deactivation, as indicated by the gap between the solid lines 215 and 220. The cycle can be repeated by activating the negative-pressure source 105, as indicated by line 220, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time, as indicated by the dashed line 225. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time, as indicated by the solid line 220, may be a value substantially equal to the initial rise time as indicated by the dashed line 225.

Figure 3:
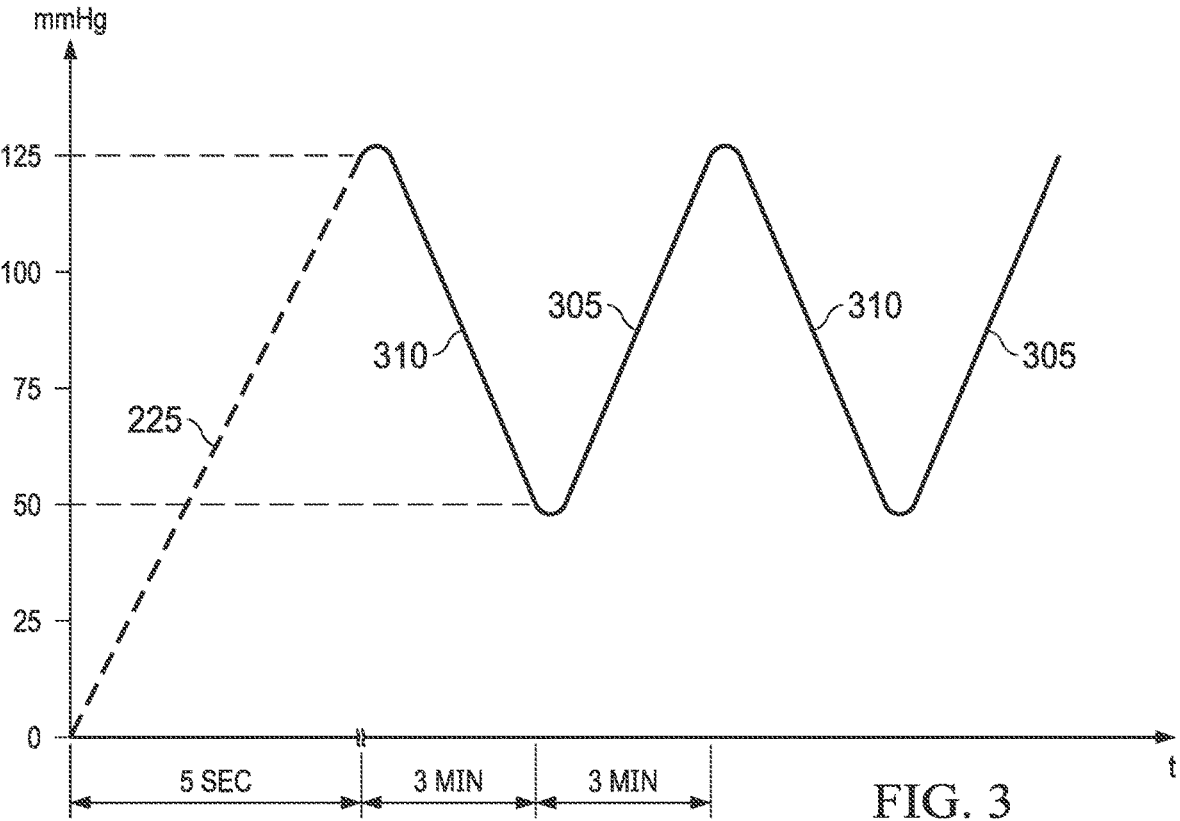
FIG. 3 is a graph illustrating additional details that may be associated with another example pressure control mode in some embodiments of the therapy system of FIG. 1.

FIG. 3 is a graph illustrating additional details that may be associated with another example pressure control mode in some embodiments of the therapy system 100. In FIG. 3, the x-axis represents time and the y-axis represents negative pressure generated by the negative-pressure source 105. The target pressure in the example of FIG. 3 can vary with time in a dynamic pressure mode. For example, the target pressure may vary in the form of a triangular waveform, varying between a negative pressure of 50 and 135 mmHg with a rise time 305 set at a rate of +25 mmHg/min. and a descent time 310 set at −25 mmHg/min. In other embodiments of the therapy system 100, the triangular waveform may vary between negative pressure of 25 and 135 mmHg with a rise time 305 set at a rate of +30 mmHg/min and a descent time 310 set at −30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 4:
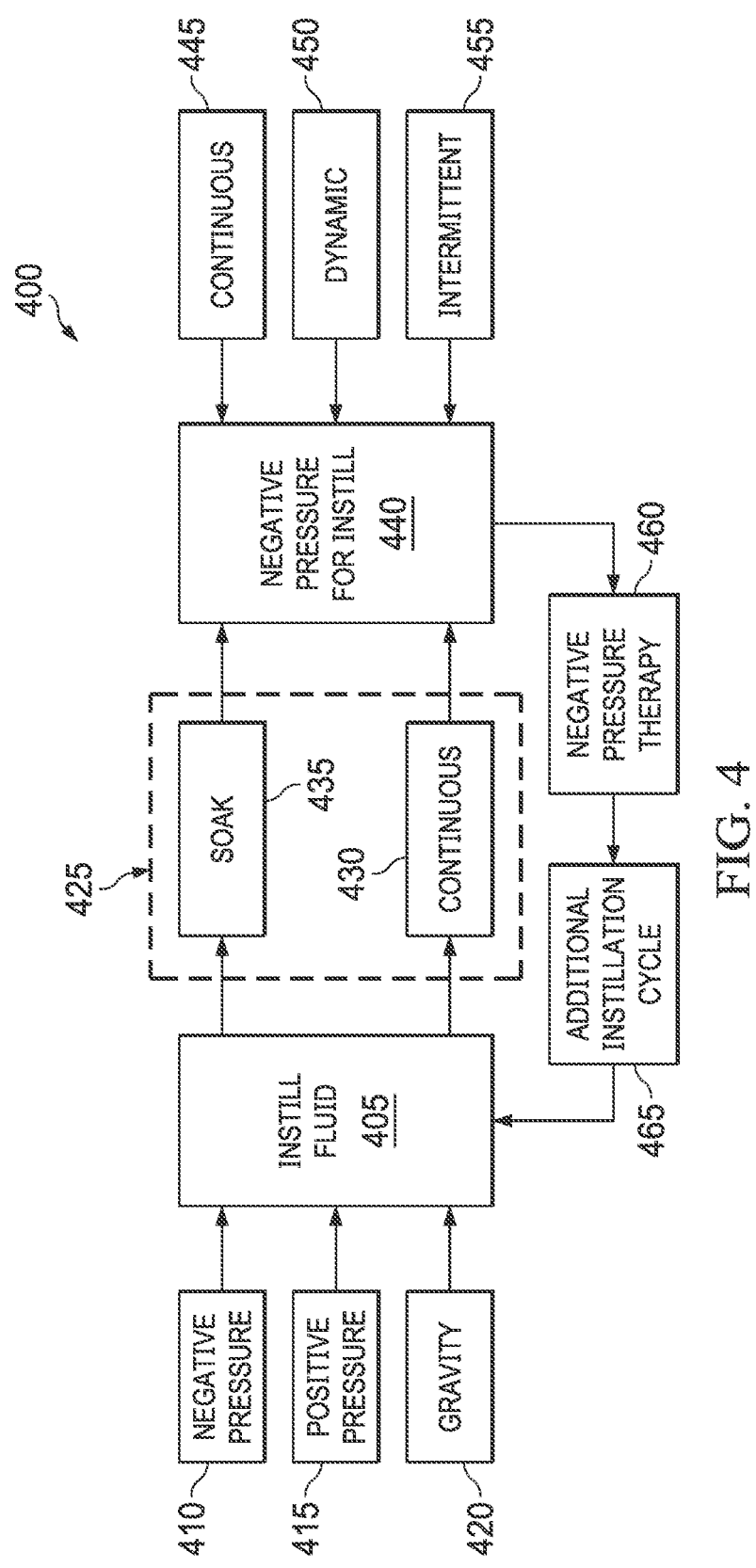
FIG. 4 is a diagram illustrating additional details that may be associated with an example embodiment of therapy system of FIG. 1.

FIG. 4 is a chart illustrating details that may be associated with an example method 400 of operating the therapy system 100 to provide negative-pressure treatment and instillation treatment to the tissue interface 120. In some embodiments, the controller 130 may receive and process data, such as data related to instillation solution provided to the tissue interface 120. Such data may include the type of instillation solution prescribed by a clinician, the volume of fluid or solution to be instilled to a tissue site ("fill volume"), and the amount of time prescribed for leaving solution at a tissue site ("dwell time") before applying a negative pressure to the tissue site. The fill volume may be, for example, between 10 and 500 mL, and the dwell time may be between one second to 30 minutes. The controller 130 may also control the operation of one or more components of the therapy system 100 to instill solution, as indicated at 405. For example, the controller 130 may manage fluid distributed from the solution source 145 to the tissue interface 120. In some embodiments, fluid may be instilled to a tissue site by applying a negative pressure from the negative-pressure source 105 to reduce the pressure at the tissue site, drawing solution into the tissue interface 120, as indicated at 410. In some embodiments, solution may be instilled to a tissue site by applying a positive pressure from the positive-pressure source 160 to move solution from the solution source 145 to the tissue interface 120, as indicated at 415. Additionally or alternatively, the solution source 145 may be elevated to a height sufficient to allow gravity to move solution into the tissue interface 120, as indicated at 420.

The controller 130 may also control the fluid dynamics of instillation at 425 by providing a continuous flow of solution at 430 or an intermittent flow of solution at 435. Negative pressure may be applied to provide either continuous flow or intermittent flow of solution at 440. The application of negative pressure may be implemented to provide a continuous pressure mode of operation at 445 to achieve a continuous flow rate of instillation solution through the tissue interface 120, or it may be implemented to provide a dynamic pressure mode of operation at 450 to vary the flow rate of instillation solution through the tissue interface 120. Alternatively, the application of negative pressure may be implemented to provide an intermittent mode of operation at 455 to allow instillation solution to dwell at the tissue interface 120. In an intermittent mode, a specific fill volume and dwell time may be provided depending, for example, on the type of tissue site being treated and the type of dressing being utilized. After or during instillation of solution, negative-pressure treatment may be applied at 460. The controller 130 may be utilized to select a mode of operation and the duration of the negative pressure treatment before commencing another instillation cycle at 465 by instilling more solution at 405.

Figure 5A:
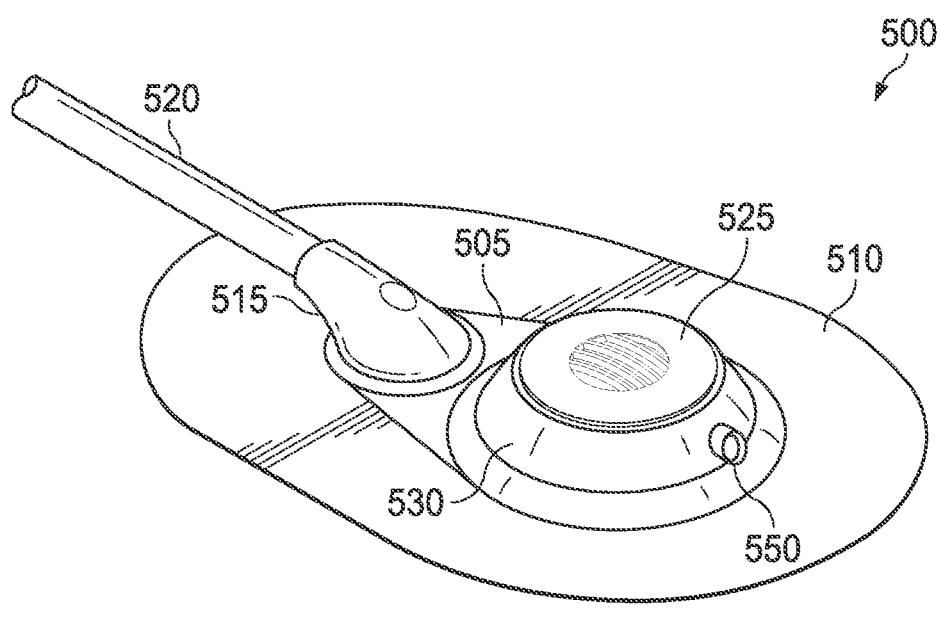
FIG. 5A is an elevated perspective view of tan embodiment of a vibration delivery system.
Figure 5B:
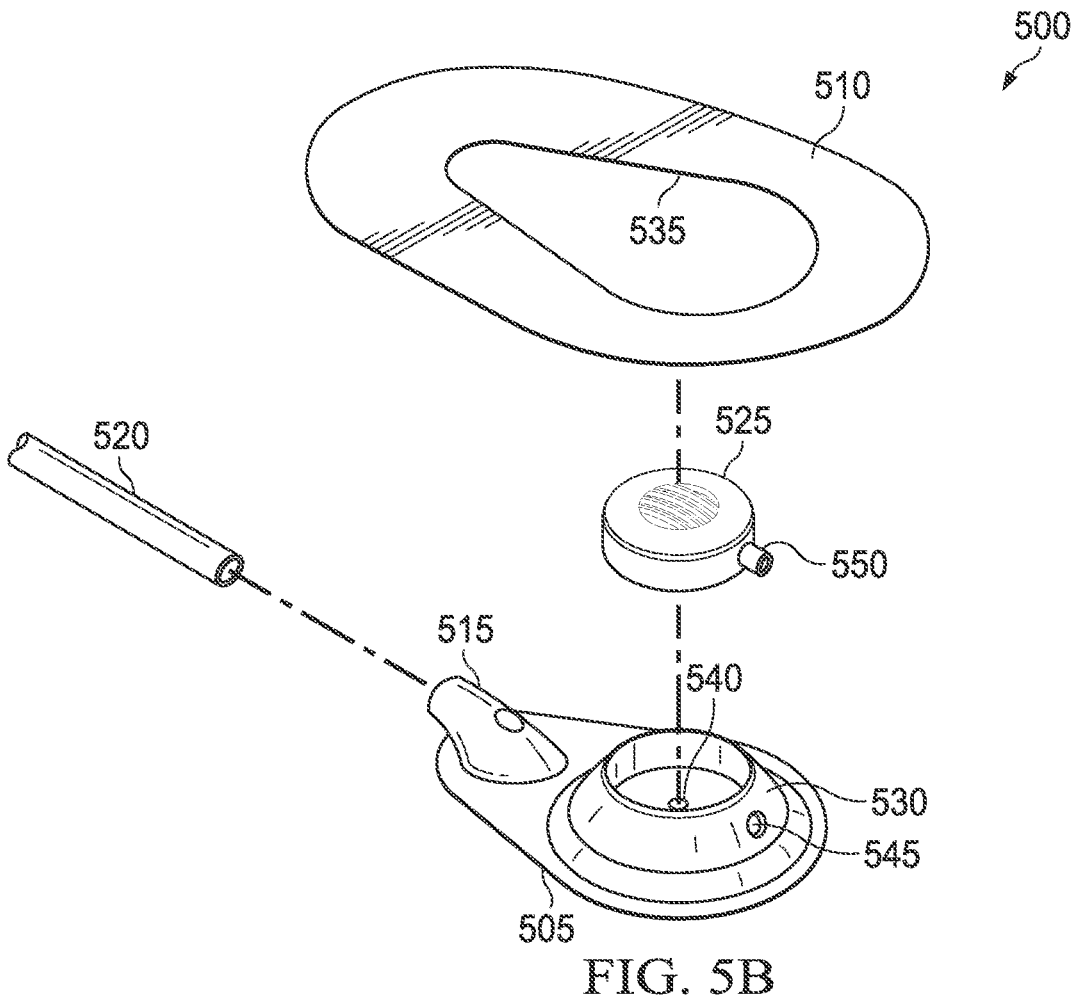
FIG. 5B is an exploded view of the vibration delivery system of FIG. 5A.

Referring now to FIGS. 5A and 5B in combination, an elevated perspective view of a vibration delivery system 500 illustrating additional details that may be associated with some example embodiments of the therapy system 100 and an exploded view of the vibration delivery system 500 are shown respectively. The vibration delivery system 500 may include a pad 505 configured for placement over a wound site. A drape ring 510 surrounds the periphery of the pad 505, and has an adherent on the wound-facing side to effectively seal the wound site from the outside environment. In certain embodiments, the drape ring 510 may adhere to a drape (not shown) that encloses the wound and adheres to the periwound area. The vibration delivery system 500 may further include a pressure port 515 coupled to the pad 505 for communicating pressure through the pad 505 to the wound. In some embodiments, a fluid conductor such as a delivery tube 520 connects to the pressure port 515 and to a negative pressure source (not shown) such as the negative-pressure source 105 for delivering negative pressure to the wound site. A vibration module 525 connects to a vibration frame 530, which in turn is coupled to the pad 505.

The drape ring 510 defines an opening 535 therein. The opening 535 is shaped to connect with the periphery of the pad 505. Preferably the drape ring 510 comprises an elastomeric material, and is conformable for placement on irregular surfaces. The drape ring 510 couples to a drape (not shown) such as the cover 125 and secures the vibration delivery system 500 to the drape. The pad 505 includes the vibration frame 530, which may be shaped to receive the vibration module 525 therein. The pad 505 defines an opening 540 for fluid communication between the vibration frame 530 and the wound site, and includes a port 545 adapted to receive a leak tube 550 of the vibration module 525.

Figure 6:
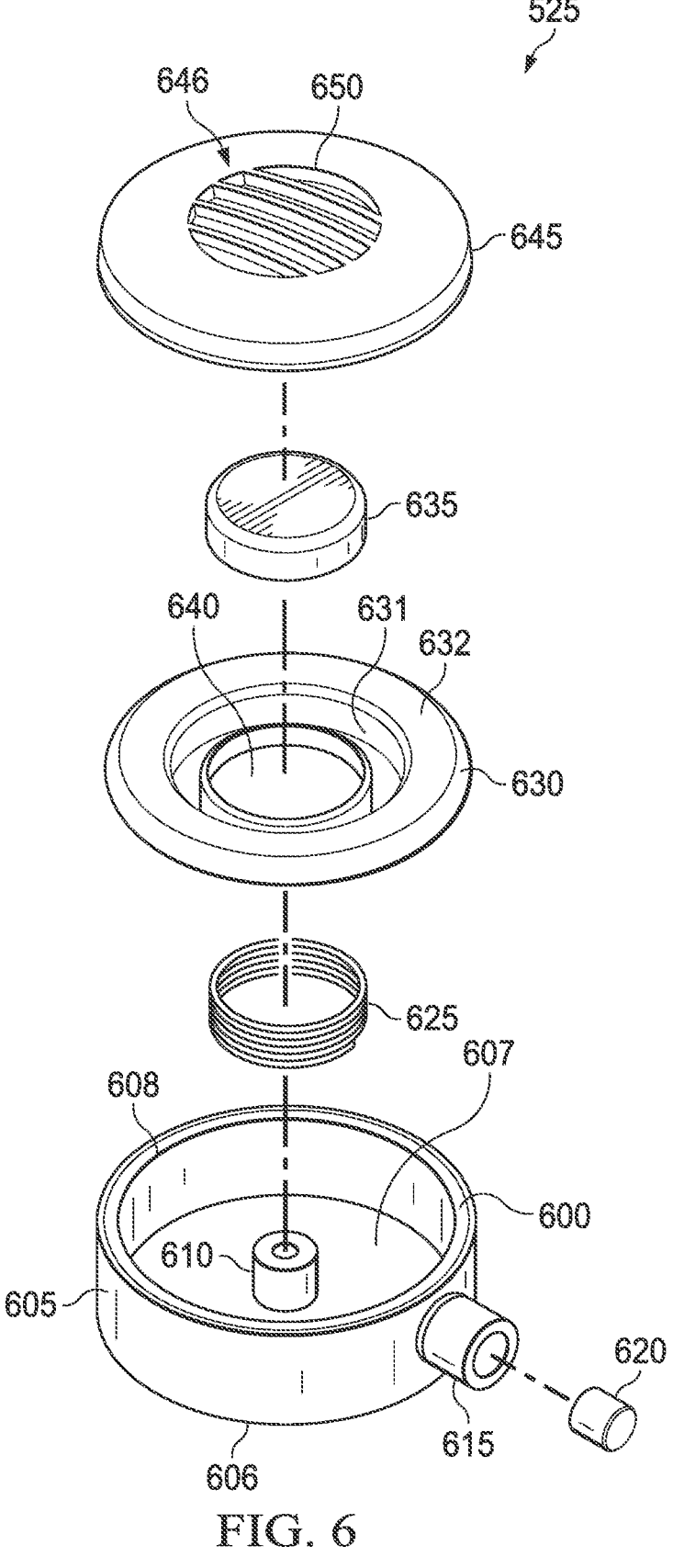
FIG. 6 is an exploded view of an embodiment of a vibration module associated with the vibration delivery system of FIGS. 5A and 5B.

Referring now to FIG. 6, an exploded view of the vibration module 525 is shown. The vibration module 525 may comprise a carrier 605 adapted to be disposed within the vibration frame 530 above the opening 540. The carrier 605 may comprise generally cylindrical walls 606 closed at one end by a base 607 forming a chamber within the carrier 605 and an opening 608 opposite the base 607. In some embodiments, the opening 608 of the carrier 605 may be concentric with the opening 540 of the vibration frame 530. The carrier 605 may further comprise a raised port 610 extending from the base 607 within the chamber of the carrier 605 towards the opening 608. In some embodiments, the raised port 610 may be adapted to be fluidly coupled to the chamber of the carrier 605 for delivering pressure and mechanical force to the vibration frame 530 and the underlying tissue interface 120. The carrier 605 may further comprise a leak conduit 615 fluidly coupled to the chamber of the carrier 605 and may contain a filter 620 adapted to regulate the amount of fluid leakage (FL) into the chamber of the carrier 605. The filter 620 may be adjustable, such that FL into the chamber of the carrier 605 may be controlled or sealed. In some embodiments, multiple filters 620 may be utilized to increase the leak rate of air into the carrier 605. The filter 620 may contain suitable material, such as for example a high density porous foam material, or a low density porous foam material, to control the leak rate as desired. The filter 620 may also be adapted to be closed to the environment through the inclusion of a valve (not shown).

The vibration module 525 may further comprise a diaphragm 630 having a center portion 631 and a peripheral portion 632 that seals or closes the opening 608 of the carrier 605. In some embodiments, the peripheral portion 632 may be flexibly coupled to the upper portion of the generally cylindrical walls 606 of the carrier 605 so that the entire diaphragm 630 is flexibly mounted with respect to the distance from the base 607. In yet other embodiments, the peripheral portion 632 may be rigidly mounted to the upper portion of the generally cylindrical walls 606 and flexibly coupled to the center portion 631 so that the entire diaphragm 630 is flexibly mounted with respect to the distance from the base 607. In some embodiments, the center portion 631 may be axially aligned with the raised port 610 and configured to move axially toward the base 607 in response to the application of negative pressure into the chamber of the carrier 605. In still other embodiments, the diaphragm may comprise a rolling diaphragm.

The vibration module 525 may further comprise a biasing element such as, for example, a coil spring 625 disposed within the chamber of the carrier 605 between the center portion 631 of the diaphragm 630 and the base 607 of the carrier 605. In some embodiments, the coil spring 625 additionally may encircle the raised port 610 while resting on the base 607 of the carrier 605. In yet other embodiments, the coil spring 625 may be a coil spring configured to bias the diaphragm 630 away from the base 607 when negative pressure is removed from the chamber of the carrier 605 in a "relaxed state" and further configured to be compressed by the diaphragm 630 when negative pressure is applied to the chamber of the carrier 605 in a "compressed state" as described further below. In some embodiments, the coil spring 625 may have a spring constant such that the coil spring 625 may be compressed a compressed distance (d1) toward the base 607 in response to the amount of negative pressure applied to the chamber of the carrier 605 while in the compressed state. In yet other embodiments, the coil spring 625 may have a spring constant that may be adjustable to vary the compressed distance (d1) in response to the negative pressure applied to the chamber of the carrier 605. In some example embodiments, the vibration module 525 may further comprise an adjustment mass 635 that may be disposed or positioned on the center portion 631 of the diaphragm 630 and operatively coupled to the coil spring 625 to vary the compressed distance (d1) of the diaphragm 630 in response to the application of negative pressure to the chamber of the carrier 605. The weight of the adjustment mass 635 may be selected to supplement the spring constant of the coil spring 625 to achieve a desired compressed distance (d1) of the diaphragm 630 in response to the application of negative pressure to the chamber of the carrier 605. The diaphragm 630 may further comprise a mass receptacle 640 disposed on the center portion 631 of the diaphragm 630 receiving the adjustment mass 635 and to hold the adjustment mass 635 in place during operation between the relaxed state and the compressed state. In some example embodiments, the vibration module 525 may further comprise a cover 645 that may be disposed over the adjustment mass 635 on the peripheral portion 632. In some embodiments, the cover 645 may be removable so that the adjustment mass 635 may be selected to achieve a desired compressed distance (d1) of the diaphragm 630. In some other embodiments, the cover 645 may comprise apertures such as, for example, openings 646 for coupling the space between the diaphragm 630 and the cover 645 to the environment. In some embodiments, the openings 646 may relieve pressure variations in the space under the cover 645 that may result from pressure differentials created by the diaphragm 630 when moving between the relaxed state and the compressed state in response to the application and removal of negative pressure from the chamber of the carrier 605.

In some embodiments, the adjustment mass 635 may be used to increase the kinetic energy of the diaphragm 630 as it contacts the raised port 610. When negative pressure is applied to the chamber of the carrier 605, the diaphragm 630 compresses the coil spring 625 as described above. The FL is adjustable such that the FL into the chamber of the carrier 605 causes the diaphragm 630 to slightly decompress and move away from the raised port 610, but the ongoing negative pressure recompresses the diaphragm 630 against the raised port 610. The ongoing intermittent contact of the diaphragm 630 and the raised port 610 generates a vibration. The application of the adjustment mass 635 to the diaphragm 630 may be used to increase or decrease the force between the diaphragm 630 and the raised port 610, and will correspondingly increase or decrease the vibration frequency and amplitude.

Figure 7A:
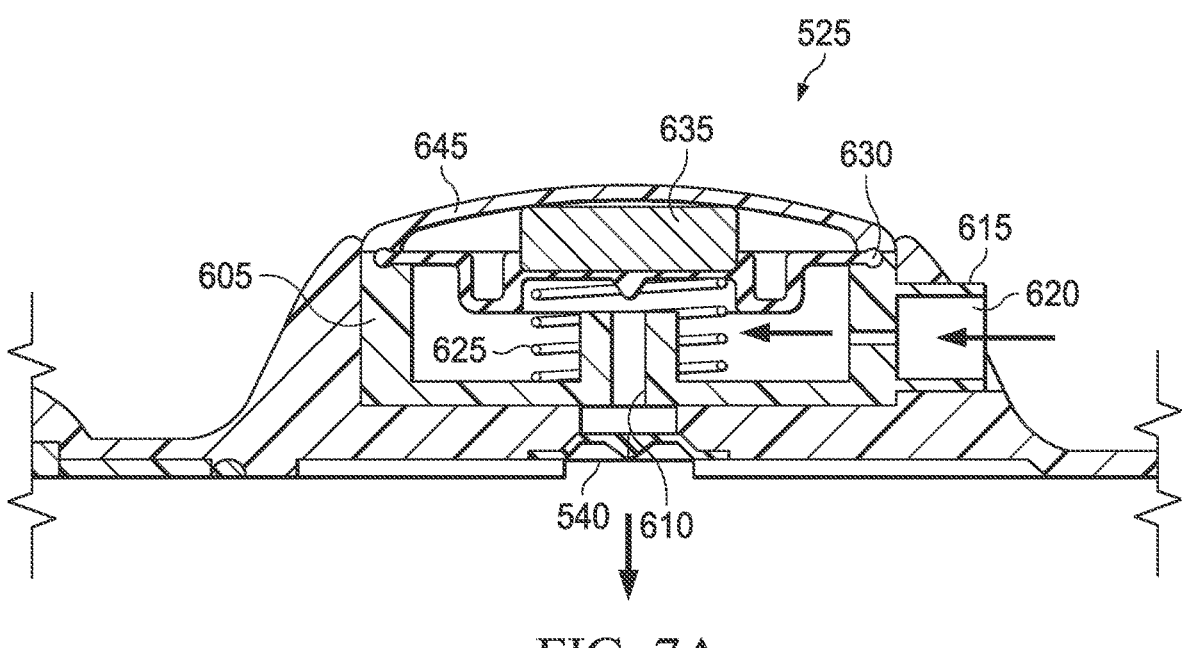
FIGS. 7A and 7B are cross-sectional views of the vibration module of FIG. 6 as shown in a "relaxed state" and in a "compressed state", respectively.
Figure 7B:
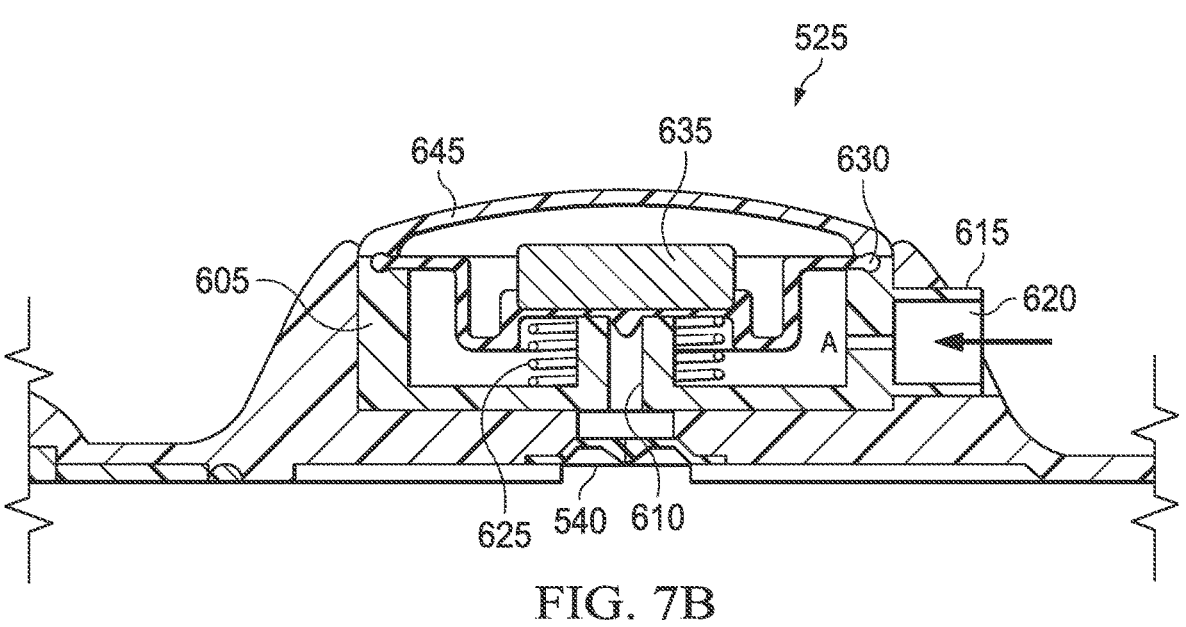

Referring now to FIGS. 7A and 7B in combination, a cross-sectional view of the vibration module 525 of FIG. 6 is shown in a "relaxed state" and in a "compressed state," respectively. When the negative-pressure source 105 is activated, air from within the chamber of the carrier 605 is pulled through the raised port 610 and through the opening 540 into the wound site. At the same time, air enters the carrier 605 through the leak conduit 615 and the filter 620 in an attempt to equalize the pressure. Because the filter 620 slows the amount of air that can be introduced from the environment into the carrier 605, the coil spring 625 compresses, ultimately until the diaphragm 630 contacts the raised port 610. The impact of the diaphragm 630 having the adjustment mass 635 disposed thereon against the raised port 610 generates a mechanical force between the diaphragm 630 and the raised port 610.

In FIG. 7B, the coil spring 625 is in the "compressed state," such that the diaphragm 630 abuts the raised port 610. The leak rate of the leak conduit 615 can be set to prevent state system pressure equalization between the chamber of the carrier 605 and the environment, such as by increasing the pore size of the filter 620, increasing or decreasing the adjustable mass 635, varying the amount of negative pressure or selecting a different spring constant for the coil spring 625. Because of the varying pressure in the chamber of the carrier 605, the diaphragm 630 continuously vibrates against the raised port 610 as it tries to reach equilibrium, and generates mechanical force, which may be translated to the dressing 110 and the wound site. When the negative-pressure source 105 is deactivated and negative pressure is removed from the chamber of the carrier 605, allowing the chamber and the environment to equalize, the coil spring 625 expands and pushes the diaphragm 630 away from the raised port 610, thus returning to the "relaxed state" shown in FIG. 7A.

The vibration force resulting from the transfer of kinetic energy from the vibration module 525 and pad 505 to the dressing 102 and wound site has beneficial properties. The vibration force functions to relieve any blockages in the dressing 102 or fluid conductor such as the delivery tube 520, thereby improving exudate flow through the pressure port 515 and the delivery tube 520 or clearing blockages that may occur in the dressing 102. Such blockages may be caused by debris, fluid coagulation or biofilm formation and combinations thereof. The vibration force may also be set sufficient enough to create enough energy to actively debride the wound, as the vibration force may cause the dressing 102 to vibrate, which in turn if the force is great enough, translate from the dressing 102 to the wound site. The resultant vibration at the wound site, if strong enough, may actively debride the tissue.

Figure 8:
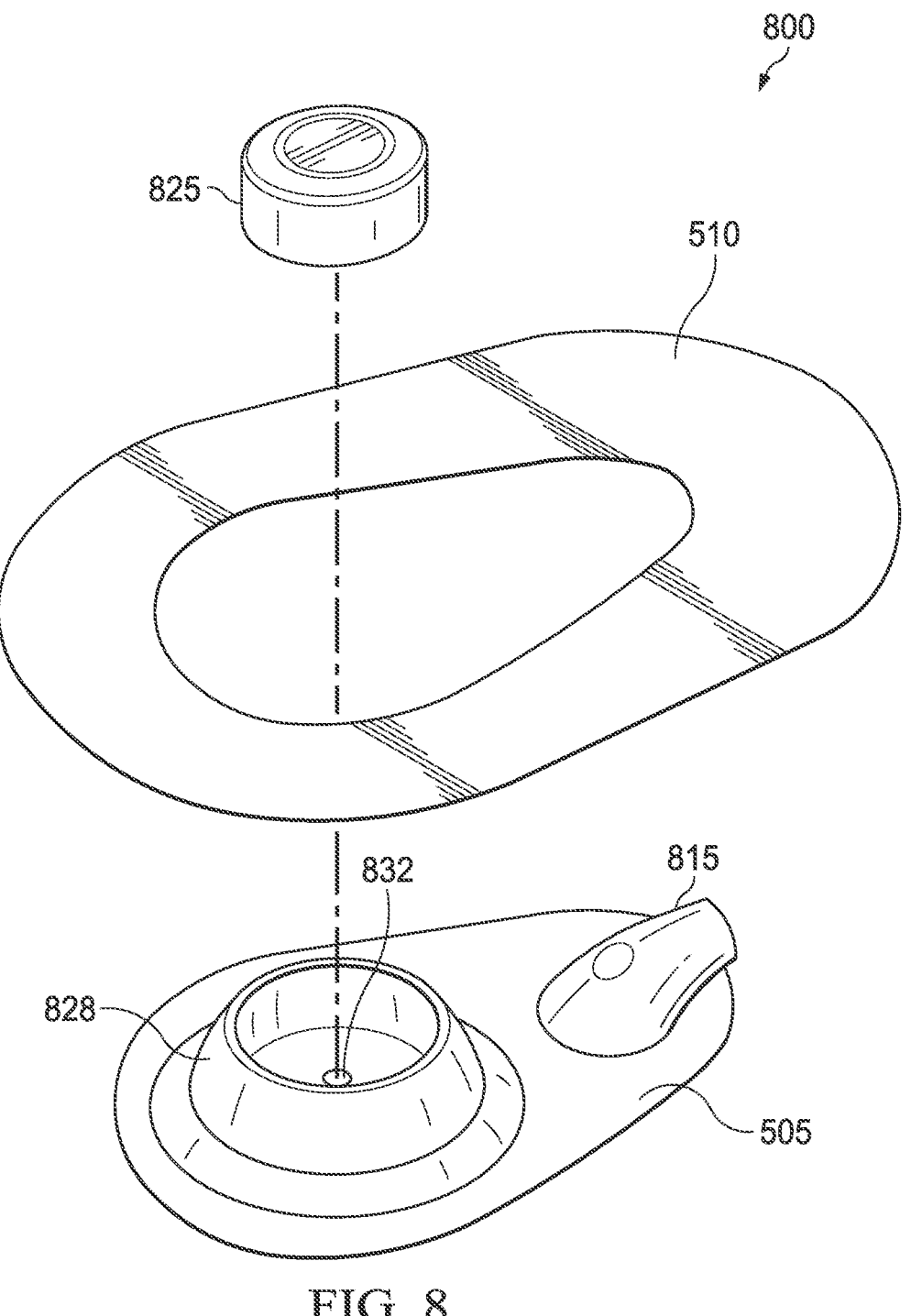
FIG. 8 is an elevated perspective exploded view of an embodiment of a vibration delivery system.

Referring now to FIG. 8, an elevated perspective view of a vibration delivery system 800 illustrating additional details that may be associated with some example embodiments of the therapy system 100 and the vibration delivery system 500. The vibration delivery system 800 may include the pad 505 configured for placement over a wound site. The drape ring 510 surrounds the periphery of the pad 505, and may have an adherent on the wound-facing side to effectively seal the wound site from the outside environment. In certain embodiments, the drape ring 510 may adhere to a drape (not shown) that encloses the wound and adheres to the peri-wound area. The vibration delivery system 800 may further include a pressure port 815 coupled to the pad 505 for communicating pressure through the pad 505 to the wound. In some embodiments, a fluid conductor such as a delivery tube (not shown) connects to the pressure port 815 and to a negative-pressure source (not shown) such as the negative-pressure source 105 for delivering negative pressure to the wound site. A vibration module 825 connects to a vibration frame 828, which in turn is coupled to the pad 505. The vibration frame 838 has an opening 832 adapted to be fluidly coupled to the wound site.

The vibration module 825 may comprise a carrier 805 adapted to be disposed within the opening 832 of the vibration frame 530. The carrier 805 may comprise generally cylindrical walls 806 closed at one end by a base 807 forming a chamber within the carrier 805 and an opening 808 opposite the base 807. In some embodiments, the opening 808 of the carrier 805 may be concentric with the opening 840 of the vibration frame 530. The carrier 805 may further comprise a raised port 810 extending from the base 807 within the chamber of the carrier 805 towards the opening 808. In some embodiments, the raised port 810 may be adapted to be fluidly coupled to the chamber of the carrier 805 for delivering pressure and mechanical force to the vibration frame 530 and the underlying tissue interface 120.

Figure 9:
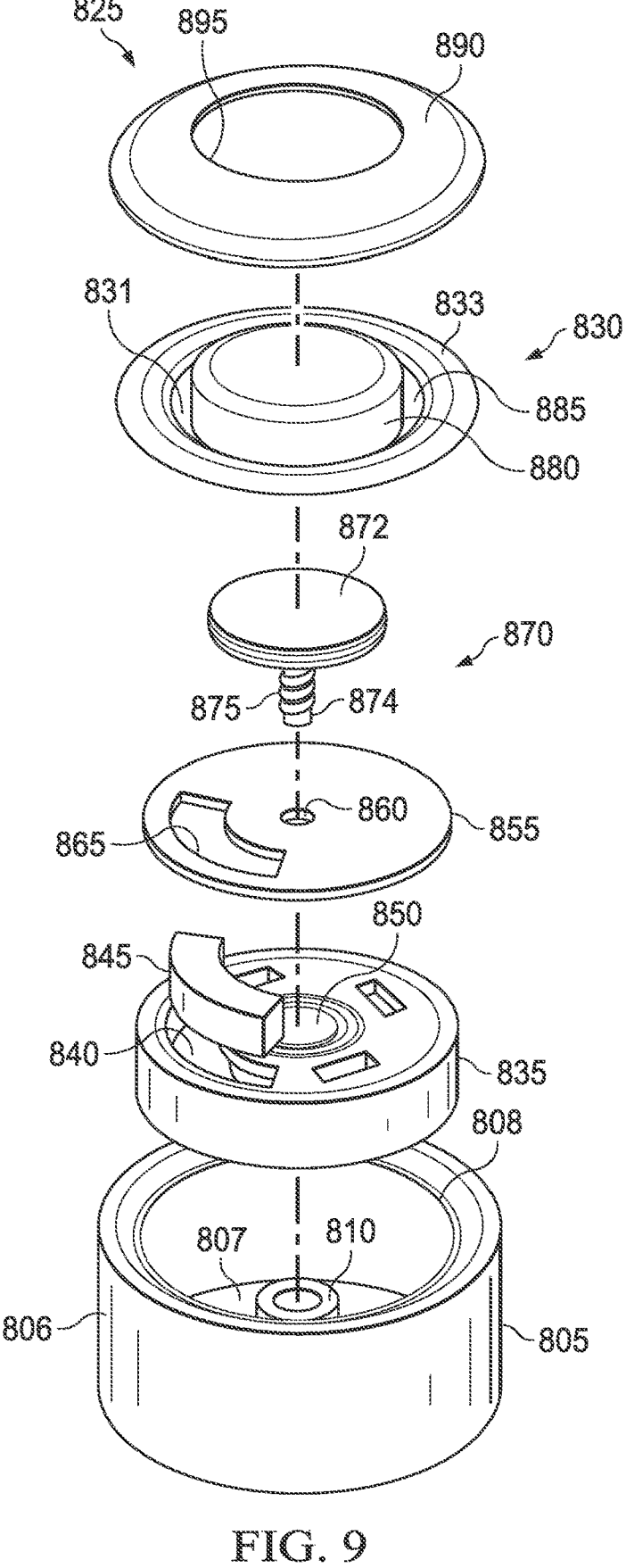
FIG. 9 is an exploded view of an embodiment of a vibration module associated with the vibration delivery system of FIG. 8.

Referring now to FIGS. 8 and 9 in combination, the vibration module 825 may further comprise a diaphragm 830 having a center portion 831 and a peripheral portion 833 that seals or closes the opening 808 of the carrier 805. In some embodiments, the peripheral portion 833 may be flexibly coupled to the upper portion of the generally cylindrical walls 806 of the carrier 805 so that the entire diaphragm 830 is flexibly mounted with respect to the distance from the base 807. In yet other embodiments, the peripheral portion 833 may be rigidly mounted to the upper portion of the generally cylindrical walls 806 and flexibly coupled to the center portion 831 so that the entire diaphragm 830 is flexibly mounted with respect to the distance from the base 807. In some embodiments, the center portion 831 may be axially aligned with the raised port 810 and configured to move axially toward the base 807 in response to the application of negative pressure into the chamber of the carrier 805.

In certain embodiments, the chamber of the carrier 805 may be adapted to receive a bearing 835, which is adapted to rotate within and substantially fill the chamber of the carrier 805. The bearing 835 may be adapted to define a mass opening 840 adapted to receive an eccentric mass 845 therein and to couple the bearing 835 to the eccentric mass 845. The bearing 835 further comprises a concentric opening 850 adapted to receive the raised port 810 therethrough.

A linkage 855 having an axial opening 860 and a mass coupling portion 865 engages the bearing 835 by the eccentric mass 845, which is received by the mass coupling portion 865. The axial opening 860 of the linkage 855 may be adapted to couple with a plunger 870 having a top portion 872 and a shaft 874 descending from the top portion 872. The shaft 874 may be adapted to engage the linkage 855 in a rotational relationship, such that when the plunger 870 moves through the axial opening 860, the linkage 855 and bearing 835 correspondingly rotate. Threads 875 may be incorporated on the shaft 874 to engage the linkage 855. In some embodiments the diaphragm 830 encloses the plunger 870, linkage 855 and bearing 835 within the chamber of the carrier 805.

Referring now to FIG. 9, an exploded view of the vibration module 825 is shown. In some example embodiments, the vibration module 825 may further comprise an adjustment mass 880 that may be disposed or positioned on the center portion 831 of the diaphragm 830 and operatively coupled to the plunger 870. In certain embodiments the plunger 870 may be statically affixed to the diaphragm 830. The weight of the adjustment mass 880 may be selected to move the increase or decrease the amount of force on the plunger 870 and increase or decrease rotation of the linkage 855. The diaphragm 830 may further comprise a mass receptacle 885 disposed on the center portion 831 of the diaphragm 830 receiving the adjustment mass 880 and to hold the adjustment mass 880 in place during operation. In some example embodiments, the vibration module 825 may further comprise a cover 890 that may be disposed over the adjustment mass 880 on the peripheral portion 833. In some embodiments, the cover 890 may be removable so that the adjustment mass 880 may be selected to achieve a desired force on the plunger 870. In some other embodiments, the cover 890 may comprise apertures such as, for example, opening 895 for coupling the space between the diaphragm 830 and the cover 890 to the environment. In some embodiments, the opening 895 may relieve pressure variations in the space under the cover 890 that may result from pressure differentials created by the diaphragm 830 when moving between the relaxed state and the compressed state in response to the application and removal of negative pressure from the chamber of the carrier 805.

Figure 10A:
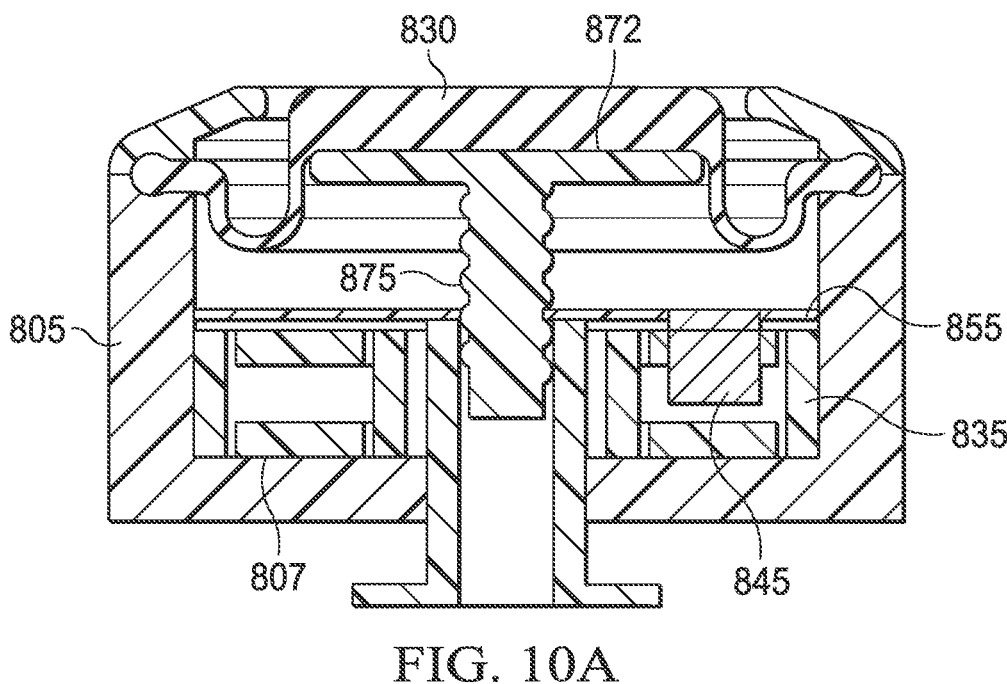
FIGS. 10A and 10B are cross-sectional views of the vibration module of FIG. 9 as shown in a "relaxed state" and in a "compressed state", respectively.
Figure 10B:
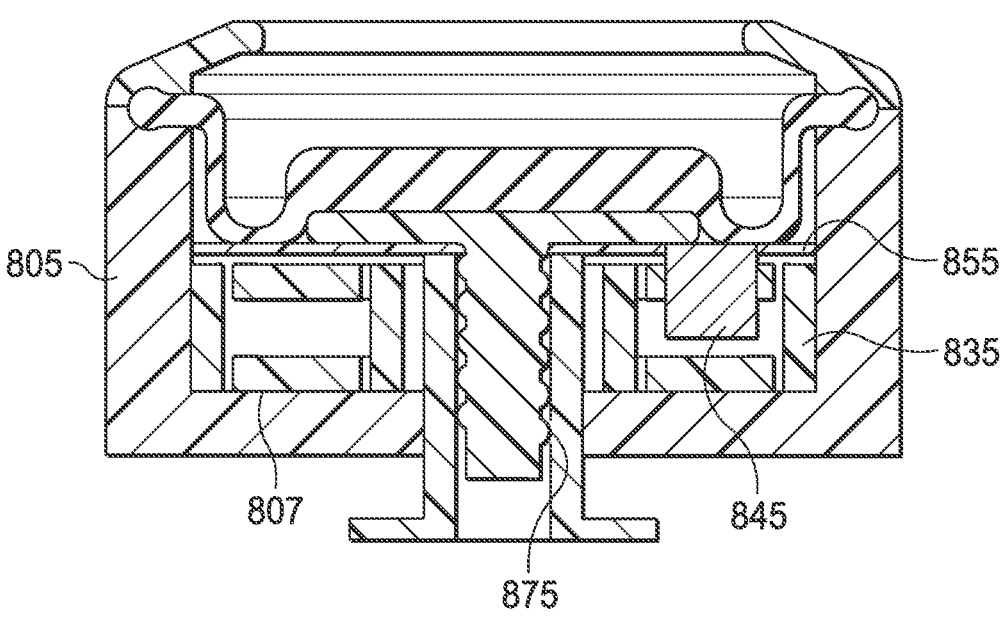

Referring now to FIGS. 10A and 10B in combination, in certain embodiments, the diaphragm 830 may comprise a rolling diaphragm, thereby acting as a biasing element. In such embodiments, the diaphragm 830 may be configured to bias the diaphragm 830 away from the base 807 when negative pressure is removed from the chamber of the carrier 805 in a "relaxed state" as shown in FIG. 10A. When negative pressure is applied to the chamber of the carrier 805, the diaphragm rolls towards the base 807 in a "compressed state," and applies force against the plunger 870 as shown in FIG. 10B. When the diaphragm 830 is in the compressed state, it effectively is primed, such that when negative pressure is removed from the chamber of the carrier

805, the diaphragm 830 ascends within the chamber to the relaxed state. The threads 875 engage the linkage 855 and rotate the linkage 855, which in turn rotates the bearing 835 having the eccentric mass 845 thereon. The rotation of the eccentric mass 845 about the plunger 870 generates a low amplitude high frequency force, which may be translated from the carrier 805 to the pad 505 and the dressing 102. In some embodiments, the force may be transmitted to the wound site.

Figure 11:
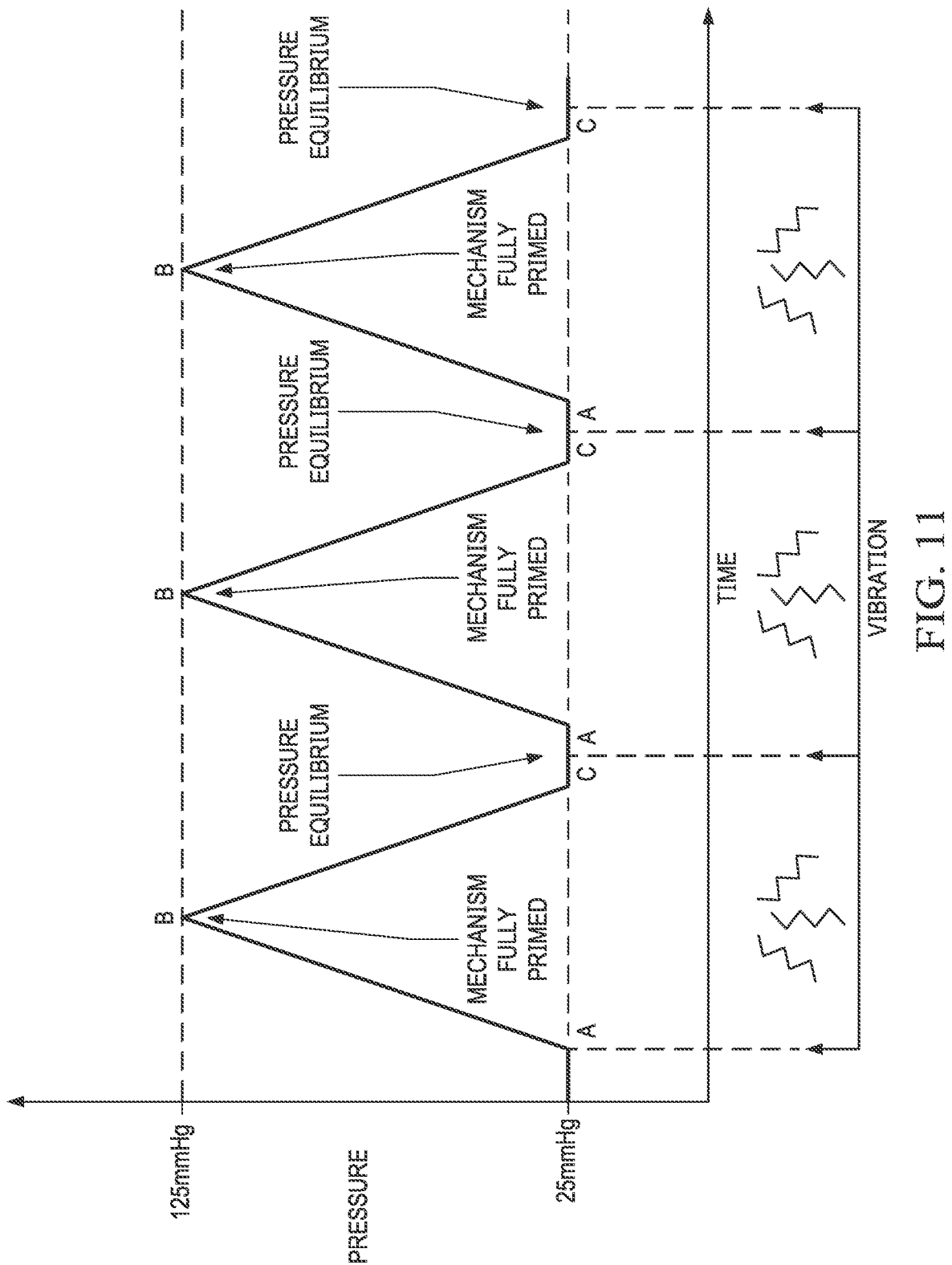
FIG. 11 is a graph illustrating additional details that may be associated with the vibration delivery system of FIG. 8.

Referring now to FIG. 11, a graph of pressure versus time is shown for operation of an exemplary embodiment of the vibration delivery system 800. The graph displays a dynamic pressure mode wave as described above with respect to FIG. 3. In operation, the vibration module 825 begins to vibrate as pressure increases from 25 mmHg to 125 mmHg at point A, though the pressure targets may be modified as desired. At 125 mmHg, the vibration module 825 is adapted to be fully primed, indicated as point B. As the pressure decreases to 25 mgHg, the vibration delivery module 825 continues to vibrate until pressure equilibrium is reached between the vibration delivery module 825 and the wound site, indicated by point C.

The systems, apparatuses, and methods described herein may provide significant advantages. For example, certain embodiments allow for debridement of the wound site depending on the kinetic force of the vibration. The translation of the kinetic force to the dressing 110 may allow the dressing 110 to vibrate against the wound site and debride the wound site. Other exemplary embodiments provide better wound exudate flow through the dressing 110 to the negative-pressure source 105, by loosening or removing blockages that may form at locations along the fluid flow pathway from the wound site to the negative-pressure source 105. Such systems, apparatuses and methods described herein may be assisted through the inclusion of a solution source for instillation. Solutions may be selected to help with exudate flow, blockage handling, and debridement.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A system for delivering negative pressure and vibrations proximate a wound site, comprising:

a dressing adapted to be fluidly coupled to the wound site and further adapted to translate vibrations to the wound site;

a pad having a pressure port adapted to be coupled to a source of negative pressure and to be fluidly coupled to the dressing, and further having a vibration frame having an opening adapted to be fluidly coupled to the wound site;

a drape adapted to cover the dressing and the pad to form a seal between the wound site and the environment, the drape having an opening exposing the vibration frame to the environment; and a vibration module supported by the vibration frame, the vibration module configured to be fluidly coupled to and pneumatically actuated by the source of negative pressure to generate vibrations, the vibration module comprising:

a carrier mounted within the vibration frame and having cylindrical walls closed at one end by a base and an opening opposite the base and concentric with the opening of the vibration frame, the base having a raised port extending into the carrier, and the cylindrical walls having a leak conduit adapted to allow a predetermined leak into the carrier;

a diaphragm sealing the opening of the carrier and being axially aligned with the raised port and configured to move axially toward the base in response to the application of negative pressure in the carrier; and a biasing element disposed within the carrier between the diaphragm and the base, the biasing element being biased to move the diaphragm away from the base when negative pressure is removed from the carrier.

2. The system of claim 1, wherein the biasing element is a coil spring.

3. The system of claim 2, wherein the coil spring is coupled to the base and the diaphragm, and encircles the raised port.

4. The system of claim 1, wherein the diaphragm is flexibly coupled to the cylindrical walls of the carrier.

5. The system of claim 1, wherein the diaphragm has a center portion and a peripheral portion coupled to the cylindrical walls and wherein the vibration module further comprises an adjustment mass disposed on the center portion and adapted to be operatively coupled to the biasing element.

6. The system of claim 5, wherein upon the application of negative pressure, the diaphragm repeatedly engages the raised port to create the vibrations in response to the predetermined leak.

7. The system of claim 6, wherein the dressing translates the vibrations to the wound site and debrides the wound site.

8. The system of claim 6, wherein the vibrations are adapted to remove fluid blockages in the dressing and the pad.

9. The system of claim 5, wherein the vibration module further comprises a cover disposed over the diaphragm forming a space in fluid communication with the environment.

10. A system for delivering negative pressure and vibrations proximate a wound site, comprising:

a dressing adapted to be fluidly coupled to the wound site and further adapted to translate vibrations to the wound site;

a pad having a pressure port adapted to be coupled to a source of negative pressure and to be fluidly coupled to the dressing, and further having a vibration frame having an opening adapted to be fluidly coupled to the wound site;

a drape adapted to cover the dressing and the pad to form a seal between the wound site and the environment, the drape having an opening exposing the vibration frame to the environment; and a vibration module supported by the vibration frame, the vibration module configured to be fluidly coupled to and pneumatically actuated by the source of negative pressure to generate vibrations, the vibration module comprising:

a carrier mounted within the vibration frame and having generally cylindrical walls closed at one end by a base and an opening opposite the base and concentric with the opening of the vibration frame, the base having a raised port extending into the carrier;

a diaphragm sealing the opening of the carrier and being axially aligned with the raised port and configured to move axially toward the base in response to the application of negative pressure in the carrier;

a bearing rotatably positioned within the carrier, the bearing defining a mass opening for receiving an eccentric mass therein and for coupling the eccentric mass to the bearing, the bearing further comprising a concentric opening adapted to receive the raised port therethrough;

a linkage having an axial opening and a mass coupling portion, wherein the eccentric mass couples to the mass coupling portion and links the linkage with the bearing; and a plunger engaged to the linkage via the axial opening and disposed between the diaphragm and the linkage;

wherein when the linkage and eccentric mass rotate about an axis of the carrier, the vibration is created.

11. The system of claim 10, where the plunger comprises a top portion and a threaded shaft descending from the top portion and engaging the linkage in a rotational relationship.

12. An apparatus for delivering negative pressure and vibrations proximate a wound site, comprising:

a pad coupled to a source of negative pressure and to a dressing, and further having a vibration frame having an opening adapted to be fluidly coupled to the wound site;

a drape adapted to cover the dressing and the pad to form a seal between the wound site and the environment, the drape having an opening exposing the vibration frame to the environment; and a vibration module supported by the vibration frame, the vibration module configured to be fluidly coupled to and pneumatically actuated by the source of negative pressure to generate vibrations, the vibration module comprising:

a cylindrical carrier coupled to the vibration frame and having a base and an opening opposite the base and concentric with the opening of the vibration frame, the carrier having a leak conduit formed in a wall of the carrier to allow a predetermined leak into the carrier;

a flexible diaphragm coupled to walls of the carrier and sealing the opening of the carrier and configured to move axially toward and engage the base in response to the application of negative pressure in the carrier to create a vibration; and a biasing element coupled to the base and the diaphragm.

13. An apparatus for delivering negative pressure and vibrations proximate a wound site, comprising:

a pad coupled to a source of negative pressure and to a dressing, and further having a vibration frame having an opening adapted to be fluidly coupled to the wound site;

a drape adapted to cover the dressing and the pad to form a seal between the wound site and the environment, the drape having an opening exposing the vibration frame to the environment; and a vibration module supported by the vibration frame, the vibration module configured to be fluidly coupled to and pneumatically actuated by the source of negative pressure to generate vibrations, the vibration module comprising:

a carrier mounted within the vibration frame and having walls closed at one end by a base and an opening opposite the base and concentric with the opening of the vibration frame, the base having a raised port extending into the carrier;

a diaphragm sealing the opening of the carrier and being aligned with the raised port and configured to move toward the base in response to the application of negative pressure in the carrier;

a bearing rotatably positioned within the carrier, the bearing defining a mass opening for receiving an eccentric mass therein and for coupling the eccentric mass to the bearing, the bearing further comprising a concentric opening adapted to receive the raised port therethrough;

a linkage having an axial opening and a mass coupling portion, wherein the eccentric mass couples to the mass coupling portion and links the linkage with the bearing; and a plunger engaged to the linkage via the axial opening and disposed between the diaphragm and the linkage and adapted to move in response to pressure from the diaphragm.

14. The apparatus of claim 12, further comprising a port extending through the base and into the carrier and adapted to engage the diaphragm upon the application of negative pressure.

15. The apparatus of claim 12, wherein the biasing element is biased to move the diaphragm away from the base when negative pressure is removed from the carrier.

16. The apparatus of claim 12, further comprising an adjustment mass coupled to the diaphragm.

* * * * *